United States Patent
Russell

(10) Patent No.: US 6,287,601 B1
(45) Date of Patent: *Sep. 11, 2001

(54) TOPICAL NITRIC OXIDE DONOR COMPOSITIONS

(75) Inventor: Meri Charmyne Russell, 206 SW. 42nd St., Des Moines, IA (US) 50312

(73) Assignee: Meri Charmyne Russell, Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/333,974

(22) Filed: Jun. 16, 1999

Related U.S. Application Data

(60) Continuation of application No. 08/914,230, filed on Aug. 19, 1997, now Pat. No. 6,045,827, which is a division of application No. 08/752,415, filed on Nov. 19, 1996, now Pat. No. 5,891,472.

(51) Int. Cl.$^7$ ...................................... A61K 9/06
(52) U.S. Cl. .......................... 424/485; 424/422; 424/424; 424/426; 424/443; 424/444; 424/450; 424/484; 424/78.02; 424/78.05; 424/718; 514/150; 514/151; 514/165; 514/166; 514/564; 514/567; 514/610; 514/611; 514/644; 514/645; 514/740; 514/741; 514/742
(58) Field of Search ..................................... 424/422–428, 424/430, 433–438, 443–450, 484–488, 59, 60, 78.02–78.07, 718; 514/150, 151, 159–166, 557, 561, 564, 610, 611, 631–638, 644, 645, 740–742

(56) References Cited

U.S. PATENT DOCUMENTS 5,891,472 * 4/1999 Russell .................................. 424/484
6,045,827 * 4/2000 Russell .................................. 424/485

* cited by examiner

*Primary Examiner*—Neil S. Levy
(74) *Attorney, Agent, or Firm*—Peppper Hamilton LLP; Gilberto M. Villarcorta; Corinne M. Pauliquen

(57) ABSTRACT

Compositions and methods of the topical treatment of equine laminitis are disclosed. In particular, combinations of a fast acting nitric oxide (NO) donor, a sustained acting NO donor and an NSAID mixed in a lipid-based carrier are described. The application of such combinations to the affected areas, e.g., the hoofs and surrounding tissues, of an equine afflicted with laminitis provides relief from the debilitating effects of this painful, often life-threatening condition.

19 Claims, 2 Drawing Sheets

TOPICAL NITRIC OXIDE DONOR COMPOSITIONS

This application is a continuation of U.S. Ser. No. 08/914,230, filed Aug. 19, 1997, now U.S. Pat. No. 6,045,827 which is a divisional of U.S. application Ser. No. 08/752,415, filed Nov. 19, 1996, now U.S. Pat. No. 5,891,472 both of which are incorporated herein by reference.

1. FIELD OF THE INVENTION

This invention relates to the treatment of equine laminitis, a very painful condition affecting the laminae of an equine. Laminitis particularly affects the area where the hoofs join the limbs, and can lead to foundering or lameness. Gone untreated, the condition can lead to the separation of the hoof from the bone and to a deterioration of an equine's overall health, including failure of internal organs following infection. The invention-relates more particularly to a composition that may be topically applied to equine hoofs and surrounding tissue and which has an unusual curative effect on circulation throughout the area. A composition and method of alleviating the negative or adverse effects of equine laminitis is, therefore, provided.

2. BACKGROUND OF THE INVENTION

Equine laminitis, which is sometimes referred to as foundering, is a common disorder that has been recognized and described in even the earliest books of veterinary medicine. In an article by Green, M. E. et al., which appeared in Equine Medicine and Surgery, Fourth Edition, Vol. II, Colahan, P. T. et al. (Eds.), American Veterinary Publications, Inc. (1991), Chapter 12, pp. 1354–1358, laminitis is described as an inflammation of the pedal laminae that form the supportive bond between the hoof and the third phalanx. Laminitis is further described as a disorder of the hoof whose cause is varied. It is a complex, multi-systemic disease affecting the digestive, cardiovascular, hemic, renal, endocrine, musculoskeletal, integumentary, and immune systems. It is characterized by multi-systemic aberrations that ultimately result in reduced capillary perfusion, ischemia, and necrosis of the laminae. These results are accompanied by pain and loss of supportive function. Acute laminitis is described as comprising the events leading up to and the onset of lameness. Acute laminitis can progress to the chronic stage. The chronic stage ensues after persistent lameness (greater than 48 hours), or when the distal phalanx deviates detectably. Chronic laminitis is a consequence of some degree of loss of integrity of the supporting digital laminae. A photograph of a horse suffering from the effects of laminitis of the forelimbs is shown on FIG. 1. Notice that the horse assumes a recumbent position in which most of the weight is placed on the hind limbs and little weight bearing pressure is exerted on the forelimbs.

There are reports of evidence that equine laminitis is caused by ingestion of too much grain; colic; retained placenta; exhaustion; ingestion of black walnut shavings; ingestion of too rich grass; excessive concussion, and/or excessive cold water. Despite the gathering of voluminous information over a period exceeding 300 years, equine laminitis still remains incompletely understood, however.

While it is possible that an equine that has been subjected to this condition can recover without intervention treatment, during the course of the disease there is substantial pain, recumbency, hoof wall deformation and even sloughing of the hooves. Several symptoms are displayed, including: a bounding digital pulse, warm feet, an abnormal gait, a shifting of weight, or some combination of some or all of these. If the animal does not recover, after the onset of lameness, the laminae deteriorate, the animal's feet are extremely painful, and the coffin bone becomes displaced. Destruction of the animal is then the only humane course of action.

Because of the serious consequences of this condition, it has been the subject of many and varied treatments over the years. In almost all cases, since the condition appears to be a function of a loss of circulation in the hoof area, the treatments have been directed to increasing the blood supply to and circulation within the hoof and adjacent tissues.

There are several different treatments that are currently being used to care for horses with laminitis. Several different vasodilators have been used in the past to treat this disorder and some are still in use. Many of them involve the use of nitroglycerin, which has been applied transdermally. Other methods use orally administered isoxsuprine, also a known vasodilator. Current therapy also includes the use of anticoagulants, such as heparin, aspirin and trental (pentoxifylline). All current therapies suffer from one or more drawbacks, including difficulty in the mode of administration of the active drug, lack of effectiveness, lack of compliance and lack of simplicity in the proposed treatment regimen.

Katsuki, S. et al., in J. Cyclic Nucleotide Res. (1977) 3:23–35, point out that the activity of a variety of smooth muscle relaxing agents, including sodium nitroprusside, nitroglycerin and sodium nitrite, may be related to their ability to increase tissue levels of cyclic guanosine monophosphate (cGMP) or to the formation of nitric oxide (NO). Other nitrogen-containing compounds may also function similarly, including hydroxylamine or sodium azide. These substances may also possess vasodilatory properties. These and other nitrogen-containing compounds may then be referred to as nitric oxide "donors" or "precursors."

It has been shown that vascular endothelial cells synthesize nitric oxide from L-arginine (L-Arg) but not D-arginine. See, Palmer R. M. J. et al., in Nature (1988) 333:664–666. This article also describes how the release of NO from endothelial cells induced by bradykinin and the calcium ionophore A23187 is reversibly enhanced by infusions of L-Arg or L-citrulline. The release of NO by certain cells can be protracted. Hence, L-Arg can be considered an NO donor or precursor, but because the conversion of L-Arg may not immediate and may occur over a protracted period of time, L-Arg can be thought of as a "slow acting" NO precursor. As used herein a "slow acting" NO precursor may provide for the release of NO in the tissues over the course of a few hours to several hours after initial exposure to the "slow acting" NO precursor. In contrast, a "fast acting" NO precursor, such as nitroglycerin or nitroprusside, generally provides almost instantaneous release of detectable levels of NO in the plasma or tissue (e.g., within about a few minutes of exposure to the "fast acting" NO precursor and lasting for several minutes). Such "fast acting" agents may be quickly depleted, however. Thus, a fast acting NO donor may be used to provide a burst of NO, while a slow acting NO donor may be used to provide a more sustained, protracted level of NO release.

An abstract by Hinckley, K. A. et al., which appeared in J. Endocrinol. (1994) 143:P103, illustrates the complexity of the aetiology of laminitis. These authors conclude that the causes of laminitis are multifactorial. These authors speak only of the intravenous administration of L-Arg.

In an editorial leader in the publication, Equine Vet. J. (1996) 28(1):1–2, Elliott, J. discusses the merits of nitric oxide treatment of laminitis. In this article, it is pointed out that NO was formerly known as endothelium derived relaxing factor, a tribute to the fact that this gas is produced continuously by the lining of blood vessels as a result of the action of an enzyme present in the endothelial cells, endothelial nitric oxide synthase or eNOS. It is thought that eNOS is activated by a rise in intracellular calcium concentration, catalyzing the conversion of L-Arg to NO and L-citrulline. The nitric oxide passes through biological membranes, binds to haem iron in the soluble enzyme guanylate cyclase (GC). The activity of GC is thus stimulated, cyclic guanosine monophosphate concentrations increase and vascular smooth muscle tone is reduced. There is speculation in this article that disruption of the blood flow to the sensitive laminae of the equine foot, which occurs in laminitis, might involve some disturbance in the L-Arg-NO pathway.

The subject of the editorial, an article by Hinckley et al. in the same issue, Equine Vet. J. (1996) 28(1):17–28, describes a treatment that uses intravenously administered L-Arg and topically applied nitroglycerin (glyceryl trinitrate or GTN). The L-Arg is administered i.v. as a 10% aqueous solution, while the GTN is provided as a 20% ointment through a patch that is positioned, using adhesive tape, over digital vessels. In particular, a laminitic pony, weighing 250 kg, received a total dose of 120 g of L-Arg or 0.48 g/kg bwt at a rate of approximately 40 mL/min (16 mg/kg bwt/min) for 30 min. The GTN patches were also applied once daily to three limbs only, 12 hours after the L-Arg infusion. Drops in heart rates were observed, including hypotension and cardiac arrhythmia, with the i.v. infusion. Some ponies showed signs of pain, sweating and shivering. The topical application of GTN patches appeared to improve the lameness of some of the treated ponies. No improvement was observed in others. Thus, it is clear that L-Arg, given intravenously, is not a particularly effective treatment. The results of the balance of this study are also mixed. There is no suggestion in this article that L-Arg should be administered in a manner other than intravenously or that any benefits may be obtained from a further pursuit of a combination treatment.

Lecithin organogels are obtained by adding a minimal amount of water to a solution of lecithin in organic solvent. Typically, a minimum amount of water is added to lecithin dissolved in an organic solvent. See, Scartazzini, R. and Luisi, P. L., in J. Phys. Chem. (1988) 92:829–833. The results of an investigation on the transdermal transport of scopolamine and broxaterol through human skin using a soybean lecithin organogel has been described. Willimann, H. et al., in J. Pharmaceutical Sci. (1992) 81(9):871–874. It was found that the rate of transdermal transport of scopolamine was about one order of magnitude higher with the organogel relative to an aqueous solution of the drug at the same concentration. However, the rate of transport of the drug was not different with the organogel compared with a pre-gelation, microemulsion of the drug (lecithin, organic solvent and drug, but no added water).

In U.S. Pat. No. 4,882,164, granted to Ferro, A. and Steffen, H., an aqueous mixed micelle solution composed of cholanic acid salts and lipids is used for the solubilization of non-steroidal anti-inflammatory drugs (NSAIDs). Cholanic acid salts include cholates, glycocholates and taurocholates. Lipids include phosphatidylcholines, especially, natural and synthetic lecithins. A formulation in accordance with the invention is described, as follows: carprofen (50 mg), L-Arg (30 mg), anhydrous glycocholic acid (88.5 mg), 40% sodium hydroxide (19 microliters), lecithin for mixed micelles (169 mg), 2N HCl (to pH 6.0) and water for injection (to make 100 mL final volume). The presence of the cholanic acid is essential to the composition described. Further, the presence of an NO precursor or vasodilator is not disclosed, taught, or suggested.

NSAIDs are compounds that are structurally different from steroids and which display an anti-inflammatory activity. NSAIDs usually contain a carboxylic acid group and are derived from acetic acid, propionic acid, butyric acid, salicylic acid and the like. Subcategories of NSAIDS, include aminoarylcarboxylic acids (e.g., enfenamine, flufenaminic acid, isonixin, niflumic acid and the like), arylacetic acids (e.g., acemetacin, alcoflenac, amfenac, 30 clopirac, felbinac, fenclofenac, ibufenac, indomethacin, isoxepac, sulindac, zomepirac and the like), arylbutyric acids (e.g., bumadizon, fenbufen, xenbucin and the like), arylcarboxylic acids (e.g., clinadac, ketorolac and the like), arylpropionic acids (e.g., benoxaprofen, carprofen, ibuprofen, ibuproxam, indoprofen, ketoprofen, naproxen, oxaprozin, protizinic acid, suprofen and the like), pyrazoles, pyrazolones and thiazinecarboxamides. Specific examples of NSAIDs include, but are not limited to, flunixin, epirizole, apazone, feprazone, ramifenazone, droxicam, aspirin, phenylbutazone, piroxicam, bendazac, ditazol, guaiazulene, oxaceprol, proxazole, tenidap and the like, or the salts thereof.

Hence, a strong need remains for an effective treatment of equine laminitis.

3. SUMMARY OF THE INVENTION

In accordance with the invention, a topical composition for the treatment of equine laminitis is described comprising a fast acting nitric oxide (NO) donor, preferably nitroglycerin, and a sustained acting NO donor, preferably L-arginine (L-Arg), dispersed in a lipid-based carrier. In a preferred embodiment of the invention, the topical composition further comprises a non-steroidal anti-inflammatory drug (NSAID). The lipid-based carrier comprises preferably a membrane forming lipid, such as a phosphatidylcholine (e.g., a naturally occurring, naturally derived, synthetic, or semi-synthetic lecithin). Preferably, the topical combination is in the form of an ointment, emulsion, creme, gel, or foam that permits the delivery of the active ingredients of the fast acting nitric oxide donor and L-Arg through the hoof, skin, or both of an affected equine.

The invention also relates to a method of ameliorating the adverse effects of equine laminitis. The method, broadly contemplated, comprises topically administering to the affected areas of an equine an effective amount of a fast acting nitric oxide (NO) donor dispersed in a lipid-based carrier. In a preferred embodiment, the method further comprises topically administering to the affected areas an effective amount of a sustained acting NO donor. Most preferably, the method even further comprises topically administering to the affected areas an effective amount of a non-steroidal anti-inflammatory drug (NSAID). The foregoing active ingredients can be administered in any sequence (i.e., sequentially) or substantially at the same time period (i.e., contemporaneously).

By utilizing the compositions and methods of the present invention, it has surprisingly been discovered that topical application directly to the affected areas of an equine afflicted with the adverse effects of equine laminitis, usually suffering from extreme pain, lameness, foundering, even partial separation of the hoof from the limb, reduced or failing organ function, poor appetite and near death, provides astounding results. In particular, treated horse or ponies exhibit remarkable signs of recovery, including regaining the ability to stand, improved posture, normal gait, improved appetite, or improved and/or stabilized organ function and generally a return to normal activities.

The present invention also contemplates a process for the preparation of a combination, which can be applied topically to alleviate the adverse effects of equine laminitis, comprising: (a) combining a first mixture comprising at least one alcoholic solvent, at least one fast acting nitric oxide (NO) donor, at least one sustained acting NO donor and at least one NSAID with a second mixture comprising at least one membrane forming lipid and at least one biocompatible organic solvent; (b) admixing to the resulting mixture of step (a) an amount of a third mixture comprising water and a surfactant effective to provide a combination having a creamy texture.

It is therefore a primary object of this invention to provide a novel treatment for equine laminitis.

It is another object of this invention to provide a novel composition that is suitable for topical application as a treatment for equine laminitis.

It is a further object of this invention to provide a method of treating laminitis comprising topically applying an effective amount of a combination or composition that is effective for the treatment of equine laminitis.

Other and additional objects will become apparent to those of ordinary skill from a consideration of general and specific descriptions provided in this specification.

4. BRIEF DESCRIPTION OF THE DRAWINGS

5. DETAILED DESCRIPTION OF THE PREFERRED EMBODIMENTS

5.1. Glossary

Figure 1:
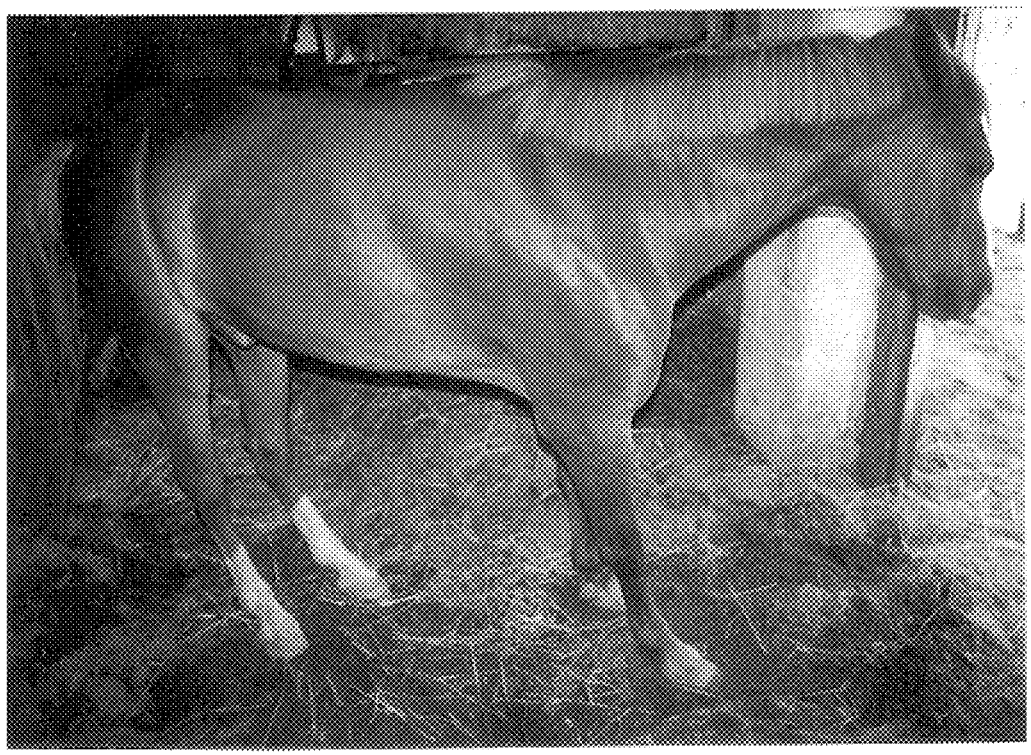
FIG. 1 illustrates a pony suffering from the adverse effects of equine laminitis (recumbent).

Nitric Oxide (NO) Donor—Any substance that is converted into, degraded or metabolized into, or provides a source of in vivo nitric oxide or NO. A "fast acting" NO donor is a nitric oxide donor that gives rise to the in vivo production of NO in or around the affected areas, tissues, hoofs, limbs, etc. of the afflicted equine within about one minute to within about ten minutes of topical application of the fast acting NO donor on the affected areas, tissues, hoofs, limbs, etc. of the afflicted equine. A "sustained acting" NO donor is a nitric oxide donor that gives rise to the in vivo production of NO in or around the affected areas, tissues, hoofs, limbs, etc. of the afflicted equine within about thirty minutes to within about a few to several hours (e.g., two, four, six, or eight hours) of topical application of the sustained acting NO donor on the affected areas, tissues, hoofs, limbs, etc. of the afflicted equine.

Lipid-Based Carrier—Any carrier, preferably a pharmacologically acceptable carrier, which is comprised of lipid or fatty components, especially those having a hydrophobic moiety and a hydrophilic moiety, and which enables the transdermal transport of an active ingredient from the surface of the skin to the regions of the body below the skin. Once below the skin, the active ingredient(s) may remain localized in or around the region(s) to which the combination or composition of interest, which is partially comprised of the lipid-based carrier, has been applied. Alternatively, the active ingredient(s) may become available systemically. A preferred class of lipids, include those that form membranes, bilayers, vesicles, liposomes and the like, particularly biological membranes. Examples of such membrane-forming lipids include but are not limited to phospholipids, glycolipids and cholesterol-type lipids. Preferred lipids include phosphatidyl choline, phosphatidyl serine, phosphatidyl inositol, phosphatidyl inositol and the like.

Biocompatible Organic Solvent—An organic solvent, typically comprised of esters of fatty acids. The fatty acids contain long chain saturated or unsaturated aliphatic groups having about 8–50 carbon atoms, preferably about 12–30, more preferably about 14–24 carbon atoms, most preferably about 16 to about 18 carbon atoms. Examples of fatty acids include lauric, myristic, palmitic, stearic, arachidic, behenic, lignoceric, palmitoleic, oleic, linoleic, linolenic, arachidonic acid and the like. The alcohol portion of the ester group is generally a linear or branched lower alkyl group comprising about 1–8 carbon atoms. Examples of the alcohol portion include methanol, ethanol, propanol, isopropanol, butanol, isobutanol, sec-butanol, tert-butanol, pentanol, isopentanol, hexanol, heptanol, octanol, isooctanol, cyclooctanol and the like. Accordingly, preferred esters include but are not limited to ethyl palmitate, ethyl myristate, ethyl oleate, isopropyl palmitate, isopropyl myristate, isopropyl oleate, and the like. Other biocompatible organic solvents may include isooctane and cyclooctane.

Second Hydroxyl Group Containing Aliphatic Organic Solvent—An organic solvent containing a hydroxyl group, including but not limited to those described in the preceding paragraph relating to the "alcohol portion of the ester group."

Surfactant—Any compound or surface active agent that reduces surface tension when dissolved in water or water solutions, or which reduces interfacial tension between two liquids, or between a liquid and a solid. Surfactants suitable for use in the present invention include ionic and non-ionic detergents, dispersing agents, wetting agents, emulsifiers and the like. Examples of surfactants include but are not limited to the sodium salt of an N-(alkylsulfonyl)glycine (EMULSIFIER STH), the salts of linear alkyl sulfonates (LAS), the salts of alkyl benzene sulfonates (ABS), the sodium salt of dodecylsulfate (SDS), a nonionic series of 28 related difunctional block-polymers terminating in primary hydroxyl groups with molecular weights ranging from about 1,000 to over about 15,000, polyoxyalkylene derivatives of propylene glycol (PLURONIC), and the like. The surfactant used in the present invention is preferably pharmaceutically acceptable and biodegradable.

5.2. The Topical Composition

As described above, the present invention is directed to a topical composition for the treatment of equine laminitis. In a particular embodiment of the invention, the topical composition comprises a fast acting nitric oxide (NO) donor and a sustained acting NO donor. In a preferred embodiment, the topical composition further comprises a non-steroidal anti-inflammatory drug (NSAID). For maximizing the effectiveness of the topical composition of the present invention, the active ingredients, such as nitroglycerin, L-Arg and ketoprofen (a fast acting NO donor, a sustained acting NO donor and an NSAID, respectively) are dispersed, optionally with other active or non-active ingredients, thickeners, emollients, fillers, etc., are dispersed in a lipid-based carrier.

The lipid-based carrier is preferably a membrane forming lipid, such as phosphatidyl choline, phosphatidyl serine, phosphatidyl inositol, phosphatidyl ethanolamine, or the like. The preferred membrane lipid comprises lecithin, as already described above. Hence, in a particular embodiment of the invention, the lipid-based carrier comprises at least one membrane forming lipid, at least one first biocompatible aliphatic organic solvent comprising 8–50 carbon atoms, at least one second hydroxyl group containing aliphatic organic solvent comprising 1–8 carbon atoms and at least one surfactant.

Typically, phospholipids suitable for the present invention are derived from glycerol (e.g., a phosphoglyceride), sphingosine, or other simple or complex alcohols, including but not limited to serine, glucose, galactose, ethanolamine, choline, inositol, mannitol and the like. The fatty acid portion of the lipid may comprise typically of about 14 to about 24 carbon atoms, more typically about 16 to about 18 carbon atoms, in particular, palmitate, oleate, or myristate. Preferred lipids include sphingomyelin, cerebroside, cholesterol, cholic acid, or phosphatidyl choline, phosphatidyl ethanolamine and the like. More preferably, the lipid-based carrier is comprised of lecithin, ether naturally occurring, naturally derived, synthetic, or semi-synthetic. A pure lecithin is comprised of a phosphatidyl choline. That is, lecithins are mixtures of diglycerides of fatty acids linked to the choline ester of phosphoric acid. Lecithins may also be classified as phosphatides, as well as phosphoglycerides.

A fast acting NO donor according to the invention may be selected from nitroglycerin, hydroxylamine, a nitrite, a nitroprusside, an azide, or a salt thereof. The sustained acting NO donor according to the invention may in turn be selected from L-Arg, derivatives thereof, analogs thereof and the like.

Particular NSAIDs suitable for use in the present invention include those derived from acetic acid, propionic acid, butyric acid, salicylic acid and the like. Also, suitable are those NSAIDs derived from an aminoarylcarboxylic acid, arylcarboxylic acid, arylacetic acid, arylpropionic acid, arylbutyric acid, pyrazoles, pyrazolones, thiazinecarboxamides and the like. Most preferably, the NSAID selected is ketoprofen, ibuprofen, or naproxen. Additional NSAIDs are described in the Background Section, above.

In a preferred embodiment of the invention, the topical composition comprises about 0.5 to 3% by weight nitroglycerin and about 6 to 20% by weight of L-Arg, based on the weight of the total composition. More preferably, the topical composition comprises about 1.0 to 2.4% by weight nitroglycerin and about 10 to 15% by weight of L-Arg, based on the weight of the total composition. In yet another embodiment, the topical composition comprises about 5 to 16% by weight nitroglycerin, based on the weight of L-Arg present in the total composition, more preferably about 7 to 8% by weight nitroglycerin, based on the weight of L-Arg present in the total composition. Where the topical combination includes an NSAID, the NSAID preferably is present in an amount that is up to about 10% by weight, based on the weight of the total combination. Other active ingredients, which may also be present in the topical combination, include analgesics, topical anesthetics and the like.

As described above, the topical composition of the invention may come in any form, but preferably as an ointment, emulsion, creme, gel, or foam. What is important, however, is that the lipid-based carrier permits the delivery of the fast acting nitric oxide donor, L-Arg and other principal active ingredients through the hoof, skin, or both of an affected equine. In a specific embodiment of the invention, the lipid-based carrier further comprises at least one pharmaceutically acceptable alcohol.

Hence in a particular embodiment a topical composition is provided for the amelioration of the negative effects of equine laminitis comprising at least one fast acting nitric oxide (NO) donor, L-Arg and at least one NSAID dispersed in a lipid-based carrier comprising at least one membrane forming lipid, at least one first biocompatible aliphatic organic solvent comprising 8–50 carbon atoms, at least one second hydroxyl group containing aliphatic organic solvent comprising 1–8 carbon atoms and at least one surfactant.

5.3. The Topical Administration

The present invention is directed to a method of alleviating or ameliorating the adverse or negative effects of equine laminitis. Generally, the desired method comprises topically administering to the affected areas of an equine an effective amount of a fast acting nitric oxide (NO) donor dispersed in a lipid-based carrier. Other methods of increasing desirability include the topical administration to the affected areas an effective amount of a sustained acting NO donor and, also, the topical administration to the affected areas an effective amount of a non-steroidal anti-inflammatory drug (NSAID). Preferably, a topical composition containing a fast acting NO donor, a sustained acting NO donor and an NSAID is applied daily for a period of at least about a few weeks (e.g., for at least about one week, two weeks, three weeks, or four weeks) to a few months (e.g., for at least about one month, two months, or three months) to the affected areas of the equine. It is important to point out, however, that each of the principal active ingredients can be topically administered sequentially or more or less contemporaneously. Also, the topical composition can be applied once daily or more than once, for example, twice daily or as needed.

The daily dosage of the fast acting NO donor ranges from about 0.165 to about 0.7 mg/kg of the equine, preferably from about 0.2 to about 0.5 mg/kg of the equine, most preferably from about 0.3 to about 0.4 mg/kg of the equine. In a specific embodiment of the invention, the dose of fast acting NO donor is about 0.33 mg/kg of the equine. The daily dosage of the sustained acting NO donor ranges from about 4 to about 9 mg/kg of the equine, preferably from about 5 to about 8 mg/kg of the equine, most preferably about 6 to about 7 mg/kg of the equine. The daily dosage of the NSAID ranges from about 1.4 to about 3.2 mg/kg of the equine, preferably from about 1.7 to about 3.0 mg/kg of the equine, most preferably from about 2.0 to about 2.8 mg/kg of the equine.

When the fast acting NO donor comprises nitroglycerin and the sustained acting NO donor comprises L-Arg, the preferred dosages range from about 0.3 to about 0.4 mg/kg of the equine and from about 6.5 to about 7 mg/kg of the equine, respectively.

In a specific embodiment of the invention a method is provided of ameliorating the adverse affects of equine laminitis which comprises topically administering at least once daily to the affected areas of an equine an effective amount of a combination comprising at least one fast acting NO donor, L-Arg and at least one NSAID in a lipid-based carrier; and continuing to administer said combination until the equine exhibits signs of recovery. Such signs of recovery include but are not limited to regaining the ability to stand, improved posture, normal gait, improved appetite, or improved or stabilized organ function. Still other signs may be obtained from performing blood tests on the affected equine, including a horse, pony, donkey, ass, zebra and the like. For example the blood test could show normal creatinine or blood urea nitrogen levels, where these levels would be elevated in ill equines.

5.4. The Process of Preparing the Topical Composition

The present invention is also directed to a process for the preparation of a combination, which can be applied topically to alleviate the adverse effects of equine laminitis. In particular, the topical combination or composition is obtained by first preparing a first mixture comprising at least one alcoholic solvent, at least one fast acting nitric oxide (NO) donor, at least one sustained acting NO donor and at least one NSAID. A second mixture is then prepared, which comprises at least one membrane forming lipid and at least one biocompatible organic solvent. The first and second mixtures are then combined with mixing, preferably at or slightly below room temperature.

To the resulting mixture, which contains the principal active ingredients (e.g., fast acting NO donor, sustained acting NO donor, optionally with an NSAID), an amount of a third mixture comprising water and a surfactant is then added, which amount is effective to provide a combination having a creamy texture. The preferred surfactant is PLURONIC.

5.5. More General Aspects of the Preferred Embodiments

As stated above, in general, the contemplated composition of this invention comprises a combination of L-Arg and nitroglycerin suitably put up in the form of a creme or ointment. It may also be used in the form of a foam. Suitable foams, ointments and cremes of topically applied therapeutic compositions are available in the art. Specifically, the topically applied compositions of this invention comprise the active ingredients as aforesaid and in addition comprise non-active components, such as a suitable carrier, which may be water-based or organic-based or a combination of both.

An ingredient in compositions, which are intended for topical application, may be a material that assists in causing the active ingredients to pass through the dermal layer to permit the subcutaneous attack of the condition sought to be ameliorated. Such dermal layer penetration assistants, which have been found to be useful in this invention, include membrane forming lipids and alcohols, particularly water soluble alcohols, and other mutual solvents that cause the normally water insoluble active ingredients to have increased water solubility and therefore increased dermal penetrability. Ethanol is one such suitable material, and is the dermal penetration assistant material of choice because it is readily available, is inexpensive and it is pharmaceutically acceptable. Ethanol is also the preferred solvent for dissolving the principal active ingredients of the present topical compositions for incorporation into the lipid-based carrier.

Another common constituent of topically applicable compositions is an emollient. Isopropyl palmitate is one example of such emollient materials. Other such materials are well known in this art and will be apparent to those of ordinary skill. Surfactants are common ingredients in cremes and ointments for transdermal delivery of medicaments. Nonionic, cationic and anionic surfactants are all considered to be suitable for use in the preparation of the topically applied composition of this invention. One suitable surfactant is a commercially available material sold under the name PLURONIC. Others will be known to the person of ordinary skill in this art.

It is considered to be within the scope of this invention to provide additional therapeutic agents in the topically applied composition hereof in order to treat specific conditions that often accompany equine laminitis. This condition is painful. It is therefore appropriate to include topical anesthetics in the inventive compositions. Topical analgesics are suitable constituents as well. NSAIDs, such as ketoprofen and naproxen, are useful additions to the creme and/or ointment compositions of this invention. Further, thickening agents are a useful part of the compositions of this invention. Hydroxymethyl or hydroxyethyl cellulose and the like can be used as thickening agents.

Cremes and ointments are known to require a combination of ingredients to balance the physical properties and to act as an effective carrier and delivery system for the medicaments that are incorporated therein. Where the topically applied composition of this invention is put up in the form of a foam, it is suitable to include conventional pharmaceutically acceptable blowing agents in the product. Suitably butane, propane, pentane and mixtures thereof have been found to be useful. These gases are relatively inert materials that have been used to make foams in the past, and they will be useful in the invention. Suitably, the volatile compound, such as a light hydrocarbon or carbon dioxide, is incorporated into the composition of this invention in a pressurized contained, such as a conventional aerosol can. When the composition is released, the light hydrocarbon blowing agent expands and converts the composition of this invention into a foam for topical application.

The active ingredients of the topically applicable compositions of this invention, illustrated by nitroglycerin and L-Arg, are suitably used in amounts of about 0.5 to about 3% by weight of nitroglycerin and about 5 to about 25% by weight of L-Arg, based on the weight of the entire composition. It is preferred to use about 1 to about 2.5% by weight of the nitroglycerin and about 15 to about 20% by weight of the L-Arg. The weight ratio of fast acting NO donor to sustained acting donor ranges from about 1:5 to about 1:50 for the total composition. There is preferably used about 2 to about 10% by weight of NSAID, preferably about 4 to about 8%, based on the weight of the total composition. Hence, the weight ratio of NSAID to sustained acting NO donor ranges from about 1:1.5 to about 1:5. The total amount of principal active ingredients can range from about 7.5 to about 45% by weight, preferably about 15 to about 35%, most preferably about 20 to about 30%, based on the total composition.

The ointment or salve or lotion or foam, which is to be topically applied, suitably contains up to about 23% by weight of the specific combination of nitroglycerin and L-Arg active ingredients, based on the total weight of the fully formulated topical composition, preferably up to about 16% by weight, most preferably up to about 14% by weight.

As indicated above, the effective topically applicable composition of this invention comprises a combination of a fast acting NO donor, such as nitroglycerin, azide, hydroxylamine and the like, and a more sustained, slower acting NO donor, such as L-Arg, in the proportions set forth above. When this active composition is in the form of a creme or ointment, the other conventional components of the cream or ointment include a carrier, such as water or mineral spirits, which will be the main or principal ingredient of the composition when considered on a weight or volume basis. This carrier or solvent will be present in the composition in amounts of about 40 to 90 weight percent of the whole composition, preferably about 60 to about 85 percent, more preferably about 70 to about 80 weight percent. Emollients, such as lecithin, or the like, are used in a proportion of up to about 10 weight percent based on the weight of the entire composition.

Conventional odorants, such as perfumes, and colorants, such as food dyes, can be used in their conventional proportions for their conventional purposes. Where needed, deodorants can also be used.

The proportion of the carrier materials, such as water, or a mixture of water and an organic solvent, such as an alcohol, will be the conventional amount that will make a smoothly applicable creme or ointment that remains on the dermal surface for a time sufficient to enable substantially all of the active ingredients to pass out of the topical application composition and pass into active relationship with the blood vessels of the equine hoofs.

Nitroglycerin and L-Arg have been specified as the active ingredients of the compositions of this invention. It will be understood that nitroglycerin is a fast acting NO donor, an immediate vasodilator, while L-Arg must first be converted to NO before it becomes effective. Therefore, the L-Arg has a more sustained release. Other immediate and sustained release sources of NO are believed effective in combating equine laminitis by means of a topically applied composition comprising combinations described herein. The compounds that appear to be comparable to nitroglycerin and L-Arg, in that they have known tendency to release NO either rapidly/immediately, or slowly/sustained, respectively, are described herein. Others may be apparent to those of ordinary skill in the art given the descriptions provided herein. Thus, other vasodilators, such as isoxsuprine or nitroprusside may be substituted for nitroglycerin. Other NSAIDs may be substituted for the ketoprofen, such as phenylbutazone, aspirin, flurixin, ibuprofen and naproxen. Slow/sustained acting NO releasing materials, which have similar activity to L-Arg, may also be apparent to those of ordinary skill in the art considering the description presented herein.

It has been found, and this is another aspect of this invention, that the transdermal transport of pharmaceutically active components, such as the NO donors of this invention, can be substantially improved. The active ingredients, that is the nitroglycerin, the L-Arg, or either of them, plus NSAID, are first dissolved in ethanol or some other pharmaceutically acceptable solvent. Preferably this solvent is also compatible with water. This active ingredient containing solution is then converted into the topical creme or ointment by being admixed or combined with a lipid, surfactant, biocompatible organic solvent, water, thickeners, emollients, surfactants, and/or other conventional ingredients of a creme, ointment or foam. The resulting topical composition is then applied to an affected portion of the dermal layer, such as a horse's hoofs and surrounding tissue. The ameliorating affect of the creme of the invention, so prepared, is quite dramatic and is illustrated further by the Examples provided, below.

6. EXAMPLES

The following are illustrative of the compositions and methods that are contemplated by the present invention.

6.1. Preparation of PLURONIC Stock Solution

Potassium sorbate (NF, 0.3 g) and PLURONIC F127 (NF, 20 g and available from PCCA, Houston, Tex.) are combined together with purified water (q.s., to a volume of 100 mL). The resulting 20% pluronic stock solution can be kept refrigerated. Thirty percent (30%) and forty percent (40%) stock solutions can also be prepared by using 30 g and 40 g of PLURONIC F127, respectively.

6.2. Preparation of Lipid/Biocompatible Solvent Mixtures

Soya Lecithin (granular, 100 g) and sorbic acid (NF-FCC powder, 0.66 g) are dispersed in isopropyl palmitate (NF, 100 g or ca. 117 mL). The mixture is allowed to stand overnight to provide a syrupy liquid. Other biocompatible organic solvents can be used in place of isopropyl palmitate, so long as it dissolves the lecithin (e.g., commercial grade soy or egg lecithin). Examples of other suitable organic solvents include, but are not limited to, isopropyl myristate (preferably, cosmetic grade) or cyclooctane.

6.3. Preparation of Lecithin PLURONIC Gel

A lecithin pluronic gel can be prepared by combining soy lecithin (granular, 10 g) with sorbic acid (NF-FCC powder, 0.3 g) in isopropyl palmitate (NF, 10 g or 11.7 mL). The mixture is allowed to stand overnight to provide a syrupy liquid. Enough 20% pluronic stock solution is then added to the syrup to brng the final to 100 mL. To the resulting lecithin pluronic gel is added L-Arg (25 g), nitroglycerin (0.8 g) and indomethacin (10 g). The resulting mixture is mixed thoroughly.

Alternatively, 52 g of soya lecithin/isopropyl palmitate solution is mixed with 19 g of 20% pluronic stock solution. To this mixture is added ethoxy diglycol (2 g), purified water (27 g), L-Arg (15 g), ketoprofen (6 g) and nitroglycerin (1.2 g). The resulting mixture is mixed vigorously until a creamy consistency is obtained.

6.4. Preparation of Transdermal Creme

Lecithin (10 g) dispersed in isopropyl myristate (10 g) is combined with a solution comprising L-Arg (15 g), ketoprofen (6 g) and nitroglycerin (1.2 g) dissolved in ethanol (10 mL). To this mixture is added an aqueous mixture of pluronic (20 g) in water (q.s., 120 g). The combined ingredients are mixed until a creamy consistency is obtained. The resulting creme can be applied topically directly to the hoof and surrounding tissue of an equine, such as a horse, to provide a treatment for alleviating the negative effects of equine laminitis:

Other suitable formulations are provided below:

| Ingredients | Example No. | | | | | |
| --- | --- | --- | --- | --- | --- | --- |
| | 1 | 2 | 3 | 4 | 5 | 6 |
| | Amounts in Grams | | | | | |
| L-Arg | 25 | 25 | 15 | 25 | 25 | 15 |
| ketoprofen | 10 | 5 | 6 | 5 | 10 | 6 |
| ethanol (mL) | 20 | 20 | 10 | 20 | 10 | 10 |
| lecithin | 10 | 10 | 10 | 10 | 10 | 10 |
| pluronic | 20 | 20 | 20 | 20 | 20 | 20 |
| nitroglycerin | 0.6 | 1.2 | 1.2 | 1.0 | 1.2 | 2.4 |
| isopropyl palmitate | 10 | 10 | 10 | 10 | 10 | 10 |
| water, q.s. (total g) | 120 | 120 | 120 | 120 | 120 | 120 |

Other NSAIDs, such as naproxen, ibuprofen and the like, can be used in place of ketoprofen. Other fast acting NO precursors, such as nitroprusside, hydroxylamine and the like, can be used in place of nitroglycerin. Other biocompatible organic solvents, such as isopropyl myristate, cyclooctane, isooctane and the like, can be used in place of isopropyl palmitate.

6.5. Use of the Transdermal Creme on a Laminitic Pony

A foundered pony (laying down, unable to stand) is treated with about 5 g of the transdermal creme of Example 3 from Section 6.4, above, three times daily. The third phalange or P-3 is observed through the sole on both feet of the pony. The creme is applied to the coronary band and to the area at the tip of the P-3 daily for a period of three to four weeks. By about week 3, the pony is able to accept nailed-in shoes and stand straight up. This improvement is remarkable given the pony's initial breached position. By the end of the fourth week, the pony is walking freely and eating normally.

Figure 2:
FIG. 2 illustrates the pony of FIG. 1 after responding to treatment using the composition and method of the present invention (note straight front legs).
Figure 3:
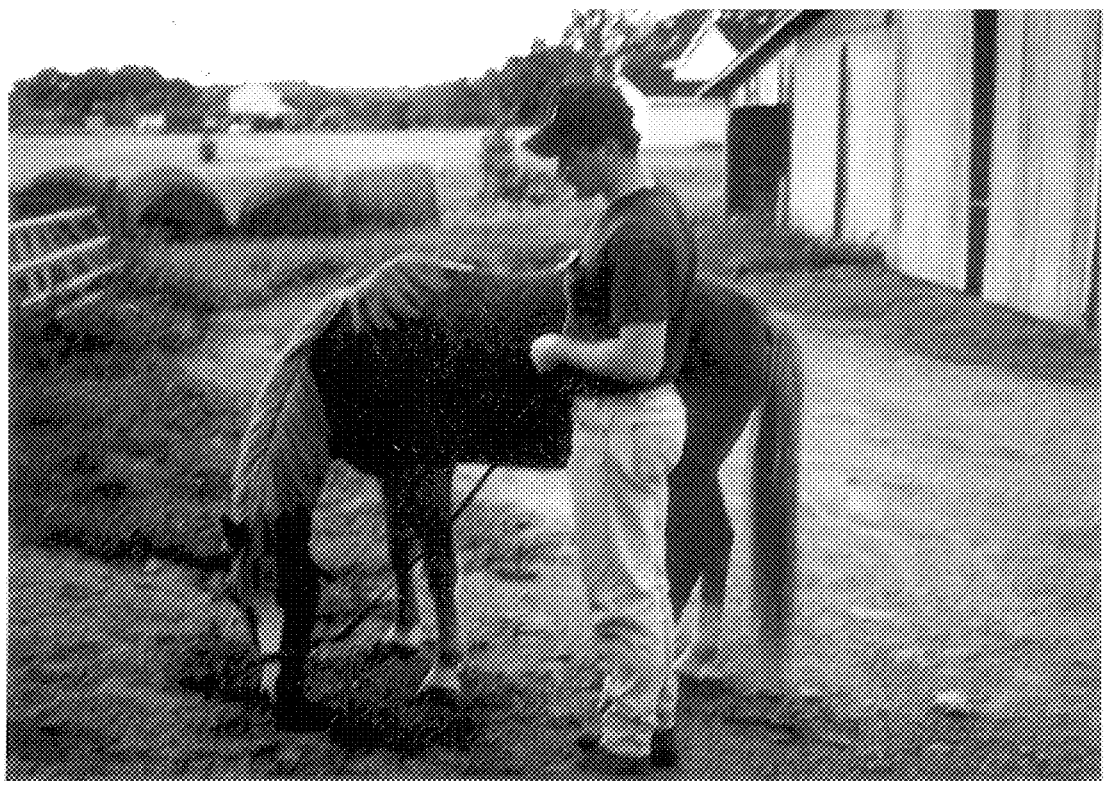
FIG. 3 illustrates the recovered pony of FIG. 2 engaged in normal activities, such as eating grass, while placing weight normally on the forelimbs and hind limbs (12 weeks from FIG. 1).

A horse, shown in FIG. 1, is exhibiting a recumbent position because of the pain associated with laminitis of the forelimbs. This horse is tested for liver and kidney function (e.g., creatinine, blood-urea-nitrogen (BUN) levels). The blood tests show greatly diminished organ function (i.e., high levels of creatinine and BUN). After one month of treatment using the transdermal creme of Example 3 from Section 6.4, the horse is able to stand upright (See, FIG. 2) and move normally (See, FIG. 3). Organ function tests that are conducted after the treatment period confirms that the horse's organs have returned to normal or near normal function.

It should be apparent to one of ordinary skill in the art that other embodiments can be readily contemplated in view of the teachings of the present specification. Such other embodiments, while not specifically disclosed nonetheless fall within the scope and spirit of the present invention. Thus, the present invention should not be construed as being limited to the specific embodiments described above, which invention is limited solely by the claims to follow.

What is claimed is:

1. A topical composition, comprising a fast acting nitric oxide (NO) donor and L-arginine (L-Arg) dispersed in a lipid-based carrier.

2. The composition of claim 1 which further comprises a non-steroidal anti-inflammatory drug (NSAID).

3. The composition of claim 1 in which said lipid-based carrier comprises a membrane forming lipid.

4. The composition of claim 3 in which said membrane forming lipid comprises a phosphatidyl choline.

5. The composition of claim 4 in which said phosphatidylcholine comprises a natural or synthetic lecithin.

6. The composition of claim 1 in which said lipid-based carrier comprises at least one membrane forming lipid. at least one first biocompatible aliphatic organic solvent comprising 8–50 carbon atoms, at least one second hydroxyl group containing aliphatic organic solvent comprising 1–8 carbon atoms and at least one surfactant.

7. The composition of claim 1 in which said fast acting NO donor is selected, from the group consisting of nitroglycerin, hydroxylamine, a nitrite, a nitroprusside, an azide, or a salt thereof.

8. The composition of claim 2 in which said NSAID is derived from acetic acid, propionic acid, butyric acid, or salicylic acid.

9. The composition of claim 2 in which said NSAID is derived from an aminoarylcarboxylic acid, arylcarboxylic acid, arylacetic acid, arylpropionic acid, arylbutyric acid, pyrazoles, pyrazolones, or thiazinecarboxamides.

10. The composition of claim 2 in which said NSAID is selected from the group consisting of ketoprofen, ibuprofen, or naproxen.

11. The composition of claim 1 which comprises about 0.5 to 3% by weight nitroglycerin and about 5 to 25% by weight of L-Arg, based on the weight of the total composition.

12. The composition of claim 1 which comprises about 1 to 2.5% by weight nitroglycerin and about 15 to 20% by weight of L-Arg, based on the weight of the total composition.

13. The composition of claim 1 which comprises a fast acting NO donor and a sustained acting NO donor in a weight ratio ranging from about 1:5 to about 1:50 for the total composition.

14. The composition of claim 2 which further comprises up to about 10% by weight of a non-steroidal anti-inflammatory drug (NSAID), based on the weight of the total composition.

15. The composition of claim 2 which comprises an NSAID and a sustained acting NO donor in a weight ratio ranging from about 1:1.5 to about 1:5 for the total composition.

16. The composition of claim 1 which is an ointment, emulsion, creme, gel, or foam.

17. The composition of claim 16 that permits the delivery of said fast acting nitric oxide donor and L-Arg through the hoof, skin, or both of an affected equine.

18. A tropical composition, comprising at least one fast acting nitric oxide (NO) donor, L-Arg and at least one NSAID dispersed in a lipid-based carrier comprising at least one membrane forming lipid, at least one first biocompatible aliphatic organic solvent comprising 8–50 carbon atoms, at least one second hydroxyl group containing aliphatic organic solvent comprising 1–7 carbon atoms and at least one surfactant.

19. A process for the preparation of a combination, comprising:

(a) combining a first mixture comprising at least one alcoholic solvent, at least one fast acting nitric oxide (NO) donor, at least one sustained acting NO donor and at least one NSAID with a second mixture comprising at least one membrane forming lipid and at least one biocompatible organic solvent; and (b) admixing to the resulting mixture of step (a) an amount of a third mixture comprising water and a surfactant effective to provide a combination having a creamy texture.

* * * * *